US012661034B2

(12) United States Patent
Melman et al.

(10) Patent No.: US 12,661,034 B2
(45) Date of Patent: Jun. 23, 2026

(54) MEASURING PRESBYCUSIS

(71) Applicant: Cochlear Limited, Macquarie University (AU)

(72) Inventors: Ryan Orin Melman, South Coogee (AU); Stefan Jozef Mauger, Macleod (AU); Riaan Rottier, Eastwood (AU); Sean Lineaweaver, Gig Harbor, WA (US)

(73) Assignee: Cochlear Limited, Macquarie University (AU)

( * ) Notice: Subject to any disclaimer, the term of this patent is extended or adjusted under 35 U.S.C. 154(b) by 497 days.

(21) Appl. No.: 18/043,989

(22) PCT Filed: Sep. 2, 2021

(86) PCT No.: PCT/IB2021/058010
§ 371 (c)(1),
(2) Date: Mar. 3, 2023

(87) PCT Pub. No.: WO2022/053915
PCT Pub. Date: Mar. 17, 2022

(65) Prior Publication Data
US 2023/0404440 A1 Dec. 21, 2023

Related U.S. Application Data

(60) Provisional application No. 63/076,596, filed on Sep. 10, 2020.

(51) Int. Cl.
*A61B 5/12* (2006.01)
*A61B 5/00* (2006.01)
*A61N 1/36* (2006.01)

(52) U.S. Cl.
CPC ............ *A61B 5/126* (2013.01); *A61B 5/6817* (2013.01); *A61N 1/36038* (2017.08)

(58) Field of Classification Search
CPC ....... A61B 5/126; A61B 5/6817; A61B 5/125; A61N 1/36038
See application file for complete search history.

(56) References Cited

U.S. PATENT DOCUMENTS 8,394,032 B2 3/2013 Cromwell et al.
9,480,418 B2 11/2016 Fausti et al.
(Continued)

FOREIGN PATENT DOCUMENTS

KR 10-2009-0082776 A 7/2009
KR 10-2015-0129661 A 11/2015

OTHER PUBLICATIONS

Lin Bian et al. Effects of low-frequency biasing on spontaneous otoacoustic emissions: Amplitude modulation. J Acoust Soc Am. Feb. 2008 ; 123(2): 887-898. doi:10.1121/1.2821983 (Year: 2008).*
(Continued)

*Primary Examiner* — Christian Jang
(74) *Attorney, Agent, or Firm* — Edell, Shapiro & Finnan, LLC

(57) ABSTRACT

Diagnosing and treating presbycusis (age related hearing loss) includes measuring basilar membrane stiffness. In an example, a low frequency component of an electrocochleo-gram stimulation signal is used to bias a region of the basilar membrane, the results of which are used basilar membrane stiffness. The resulting measurement is used to measure a subcomponent of presbycusis. Further, the measurement can be combined with known diagnostic methods to reveal or distinguish other origins of hearing loss such as strial presbycusis, sensory presbycusis, neural presbycusis, and cochlea conductive presbycusis. The relative contributions for each of the diagnosed origins of hearing loss can be determined.

29 Claims, 11 Drawing Sheets

(56)　　　　　　　References Cited

U.S. PATENT DOCUMENTS

| | | | |
|---|---|---|---|
| 2007/0219458 A1* | 9/2007 | Jeng ........................ | A61B 5/121 |
| | | | 73/585 |
| 2009/0149916 A1 | 6/2009 | Kwak | |
| 2009/0259140 A1* | 10/2009 | Buchman ............... | A61B 5/125 |
| | | | 600/559 |
| 2014/0371623 A1 | 12/2014 | Hong et al. | |
| 2017/0150282 A1 | 5/2017 | Mishra et al. | |
| 2017/0150909 A1 | 6/2017 | Dalhoff et al. | |
| 2017/0332977 A1 | 11/2017 | Dalhoff et al. | |
| 2018/0368741 A1 | 12/2018 | Wu et al. | |

OTHER PUBLICATIONS

Lichtenhan, Jeffrey. Effects of Low-Frequency Biasing on Otoacoustic and Neural Measures Suggest that Stimulus-Frequency Otoacoustic Emissions Originate Near the Peak Region of the Traveling Wave. JARO 13: 17-28 (2012) (Year: 2011).*

International Search Report and Written Opinion in counterpart International Application No. PCT/IB2021/058010, mailed Dec. 7, 2021, 6 pages.

Eun Jin Son. Recent Advances in Research of Cochlear Tonotopicity. In: Korean Journal of Otorhinolaryngology—Head and Neck Surgery, 2012, vol. 55(12), pp. 745-750 A [retrieved on Nov. 16, 2021]. Retrieved from <https://doi.org/10.3342/kjorl-hns.2012.55.12.745> pp. 745-748.

* cited by examiner

Input

302

304

Output

303

305

MEASURING PRESBYCUSIS

BACKGROUND

Field of the Invention

The present invention relates generally to the techniques for measuring presbycusis.

Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In an example, there is a method comprising: measuring a stiffness of a basilar membrane at a region of a cochlea, wherein the measuring includes: providing a sound wave having: a first frequency configured to activate the region; and a second frequency that is lower than the first frequency and is configured to bias the region; and measuring a response to the provided sound wave.

In another example, there is a method comprising: providing a first sound wave having a first frequency at a first volume to a cochlea; measuring a first response to the first sound wave; providing a second sound wave to the cochlea such that a measured second response to the second sound wave is within a threshold amount of the first response; and determine a stiffness of a basilar membrane of the cochlea based on one or more differences between the first sound wave and the second sound wave. The second sound wave includes: the first frequency at a modified volume relative to the first volume; and a second frequency, lower than the first frequency, at a second volume.

In yet another example, there is a system comprising: an electroacoustic transducer; a cochlear response sensor; and one or more processors. The one or more processors are configured to: provide a sound wave using the electroacoustic transducer and measure a response to the provided sound wave using the cochlear response sensor. The sound wave includes: a first frequency configured to activate a cochlear region; and a second frequency configured to bias the cochlear region.

BRIEF DESCRIPTION OF THE DRAWINGS

Embodiments of the present invention are described herein in conjunction with the accompanying drawings, in which.

DETAILED DESCRIPTION

Figure 1:
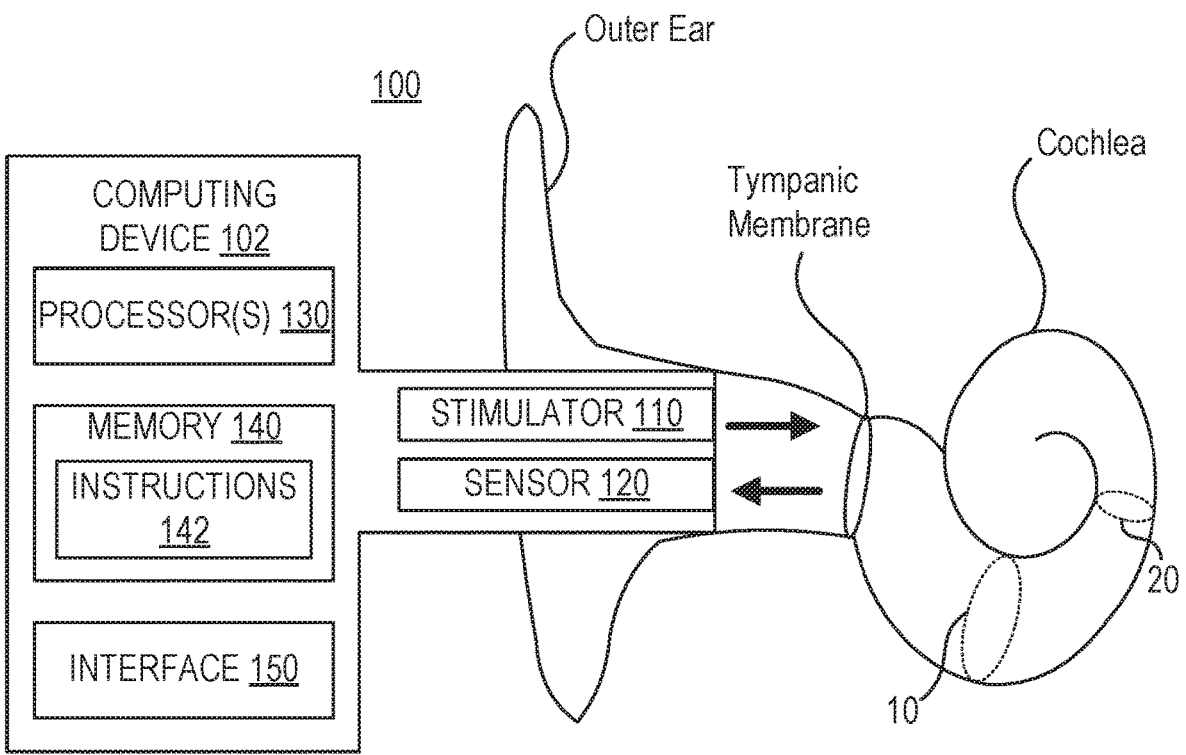
FIG. 1 illustrates an example system.

Typically, causes ("sub-components" or "sub-factors") of age-related hearing loss are bundled together under the term "presbycusis". Diagnosing and treating the overall rate of decline of hearing can be improved by measuring the sub-components. While there are at least four sub-factors of presbycusis, each of the four are not typically measured in humans. The sub-factors include strial presbycusis, sensory presbycusis, neural presbycusis, and cochlea conductive presbycusis. Strial presbycusis relates to degradation or loss of capillary area and function, which can result in reduced endolymphatic potential, loss of voltage to the cochlea outer hair cell amplifier. Strial presbycusis is associated with a hearing loss of approximately 20-60 decibels. Sensory presbycusis relates to sensory outer hair cell loss (e.g., due to noise exposure), which can result in reduced outer hair cell amplification due to loss of outer hair cells. Neural presbycusis relates to spiral ganglion neuron degradation or loss of temporal abilities, which can result in asynchronous firing of the auditory nerve. Cochlea conductive presbycusis relates to basilar membrane stiffening, which can be associated with conductive frequency specific loss. Animal research has been used to determine that these sub-factors exist and that they have different contributions to hearing and rates of decline. Strial presbycusis and sensory presbycusis can be detected based on testing outer hair cell function by measuring otoacoustic emissions or by viewing audiograms (e.g., loss at 2-4 KHz), with some research suggesting that strial and sensory presbycusis are separable with delta auditory brain response compared with delta otoacoustic emission threshold. Auditory brainstem response can be used to determine neural presbycusis. But there is currently no measure suitable in humans of basilar membrane stiffness.

Disclosed techniques include those directed to measuring basilar membrane stiffness or thickness in vivo. In an example technique, a low frequency acoustic tone is used to a constructively or destructively bias a high frequency tone bust. The ability of the low frequency tone to bias (e.g., move) the basilar membrane is used to measure the basilar membrane's stiffness. For instance, a relatively stiffer membrane will be relative less affected by the low frequency compared with a relatively more pliable membrane. An amount to which the low frequency affects the region can be used to determine the stiffness of the basilar membrane at that region. Activation is measured using an electrocochleogram. The resulting measurement is usable to not only measure stiffness, but also usable in a systemic approach to measure overall presbycusis and determining the contribution of other sub-factors of presbycusis. The results can be used to improve diagnosis or prediction of hearing loss decline, improved prediction of cochlear implant outcomes, and tailored hearing aid prescriptions.

Sounds enter the cochlea as a movement in fluid. The basal portion of the cochlea is adapted to resonate with high frequencies and is adapted to resonate with lower frequencies along the cochlea toward the apex of the cochlea. As frequencies reach their resonant place, their energy is absorbed by the basilar membrane. As such, multiple frequencies can be present at a same place in the cochlea. The relatively higher frequency can reach a resonant place where the relatively higher frequency activates neurons corresponding to that frequency. Simultaneously, a relatively lower frequency can pass the resonant place of the high frequency and continue along the cochlea. Although the low frequency does not significantly resonate the high frequency region significantly, the low frequency passing through the high frequency region does cause some movement of the basilar membrane. The extent of movement can be measured and used to determine presbycusis, such as conductive presbycusis.

As another example implementation, two tones are provided to the cochlea being measured. A higher frequency tone activates a specific cochlea region, and a lower frequency tone biases the region. First, a high frequency tone is sent at a first level (e.g., volume or intensity) having a moderate response from the cochlea (e.g., sufficient to cause a detectable response). Then, a combination tone that includes high frequency and low frequency tones are then sent such that the high frequency component of the tone (e.g., sent as a burst) overlaps constructively with the low frequency component is then sent in. When the combination is sent, the high frequency component has a reduced level (e.g., volume or intensity) relative to the first level. The low frequency tone is then increased and decreased to determine the level at which the combination tone response is the same level as the single tone response. The low frequency level or a ratio between the high frequency and low frequency level is then used as a measure of the stiffness at this frequency.

In another implementation, the tone is configured such that the low frequency tone destructively overlaps with the high frequency burst. In such an implementation, the level of the high frequency component is increased by an amount (e.g., a 20% volume increase), and the low frequency tone would be increased or decreased to find the level where combination tone response and the single tone response are similar.

In further implementations, a range of tones are used to determine the stiffness at a range of locations within the cochlea. For a single high frequency tone, a range of low frequency carriers are used to determine multiple stiffness measures as, for example, a stiffness spectrogram. In an example, the measure is conducted at a range of high frequency levels (e.g., intensity or volume) from just above threshold to moderate levels to loud levels. In an example, multiple constructive (e.g., harmonic) low frequency waves are used to build longer, squarer wave stimulus.

An example system with which example techniques described herein can be implemented is described in FIG. 1. System FIG. 1 illustrates an examples system 100. The system includes a computing device 102 being used in relation to a subject's auditory anatomy, including the outer ear, tympanic membrane, and cochlea. As illustrated, the cochlea has a first region 10 and a second region which may be affected by techniques described herein.

The illustrated computing device 102 includes a stimulator 110, a sensor 120, one or more processors 130. Although illustrated as a single device (e.g., the components are disposed in a single housing), the computing device 102 can take any of a variety of forms. In an example, the stimulator 110 and sensor 120 are disposed in a housing separate from a housing encasing the one or more processors 130, with the components being nonetheless connected via wired or wireless connection. In such an example, the stimulator 110 and the sensor 120 can be disposed in a housing configured to be at least partially disposed in or around the person's auditory anatomy. In an implementation, the one or more processors 130 are of a personal computer, server computer, hand-held device, laptop device, multiprocessor system, microprocessor-based system, programmable consumer electronic device (e.g., smart phone or tablet), network personal computer, minicomputer, mainframe computer, other computing devices, or combinations thereof.

The stimulator 110 includes one or more components configured to provide stimulation to a subject. In an example, the stimulator 110 is configured as an electroacoustic transducer, such as a driver of a headphone or speaker, that is configured to produce air-conducted vibrations directed to the subject's cochlea so as to set up waves of fluid motion of the perilymph within the cochlea that activates the hair cells inside of cochlea. In another example, the stimulator 110 is a vibratory actuator, such as a transducer of a bone conduction device, that is configured to produce bone-conducted vibrations directed to the subject's cochlea so as to set up waves of fluid motion of the perilymph within the cochlea that activates the hair cells inside of cochlea. In an example, the stimulator 110 is configured as one or more of an otoacoustic emissions system stimulator, an auditory brainstem response system stimulator, an electrocochleogram system stimulator, a delta-otoacoustic emissions system stimulator, a dual-tone-otoacoustic emissions system stimulator, or a multi-tone-otoacoustic emissions system stimulator.

The sensor 120 is one or more components configured to generate output based on detected conditions. In many examples, the sensor 120 is configured to detect otoacoustic emissions, electrocochleography responses, other responses, or combinations thereof. In an example, the sensor 120 is a cochlear response sensor configured to detect a response by a subject's cochlear system. In an example, the sensor 120 includes one or more implanted or external electrodes, such as one or more implanted electrodes of a cochlear implant (see, e.g., cochlear implant system 1210 of FIG. 12). In an example, the sensor 120 includes one or more of: an otoacoustic emissions sensor, an auditory brainstem response sensor, an electrocochleogram sensor, electrococh-leography monitor, a delta-otoacoustic emissions sensor, or a dual-tone-otoacoustic emissions sensor. In an example, the sensor 120 includes a transtympanic electrode (e.g., an electrode disposed on or configured as a needle for insertion through the subject's transtympanic membrane) or a extratympanic electrode.

The one or more processors 130 are one or more hardware or software processors (e.g., central processing units or microcontrollers) that are configured to obtain and execute instructions. The one or more processors 130 communicate with and control the performance of components of the computing device 102.

The memory 140 is one or more software- or hardware-based computer-readable storage media operable to store information accessible by the one or more processors 130. The memory 140 stores, among other things, instructions executable by the one or more processors 130 to implement applications or cause performance of operations described herein, as well as other data. The memory 140 is imple-mentable as volatile memory (e.g., RAM), non-volatile memory (e.g., ROM), transitory memory, non-transitory memory, removable memory, non-removable memory or combinations thereof. Example implementations of the memory 140 include RAM, ROM, EEPROM (Electroni-cally-Erasable Programmable Read-Only Memory), flash memory, optical disc storage, magnetic storage, solid state storage, or any other memory media usable to store infor-mation for later access. In some examples, the memory 140 encompasses a modulated data signal (e.g., a signal that has one or more of its characteristics set or changed in such a manner as to encode information in the signal), such as a carrier wave or other transport mechanism and includes any information delivery media. Examples include wired media such as a wired network or direct-wired connection, and wireless media such as acoustic, RF, infrared, other wireless media, or combinations thereof. The illustrated example of the memory 140 stores or encodes one or more instructions 142.

The instructions 142 are one or more software instructions executable by the one or more processors 130 to cause the one or more processors 130 to perform one or more actions. The instructions 142 can exist in any of a variety of forms, such as machine code, a binary executable, interpretable instructions, other forms, or combinations thereof. In some examples, one or more aspects of the instructions 142 are implemented in hardware.

The interface 150 encompasses one or more components that enable the computing device 102 to interact with one or more users or one or more other devices.

In an example, the interface 150 includes one or more networking components that communicatively couple the computing device 102 with one or more other devices. The networking components provide wired or wireless network access and can support one or more of a variety of commu-nication technologies and protocols, such as ETHERNET, cellular, BLUETOOTH, near-field communication, and RF (Radiofrequency), among others. The networking compo-nents can include one or more antennas and associated components configured for wireless communication accord-ing to one or more wireless communication technologies and protocols. In an example, where the stimulator 110 and the sensor 120 are separate from the one or more processors 130, one or more networking components are used to communicate between the components. In an example, the interface 150 includes one or more input devices over which the input from a user is received. The one or more input devices include physically-actuatable user-interface ele-ments (e.g., buttons, switches, or dials), touch screens, keyboards, mice, pens, and voice input devices, among others input devices. In an example, the interface 150 includes one or more output devices by which the computing device 102 provides output to a user, such as one or more displays, speakers, and printers, among other output devices.

In an example, the computing device 102 includes one or more components configured to operate as one or more of an otoacoustic emissions system (e.g., a distortion product otoacoustic emission), an auditory brainstem response sys-tem, an electrocochleogram system, a delta-otoacoustic emissions system, or a dual-tone-otoacoustic emissions sys-tem. Example components for operating an electrocochleog-raphy system are described in US 2017/0304632, which is titled "Electrocochleography Testing in Hearing Prosthe-ses", and which is hereby incorporated herein by reference in its entirety for any and all purposes.

Figure 2:
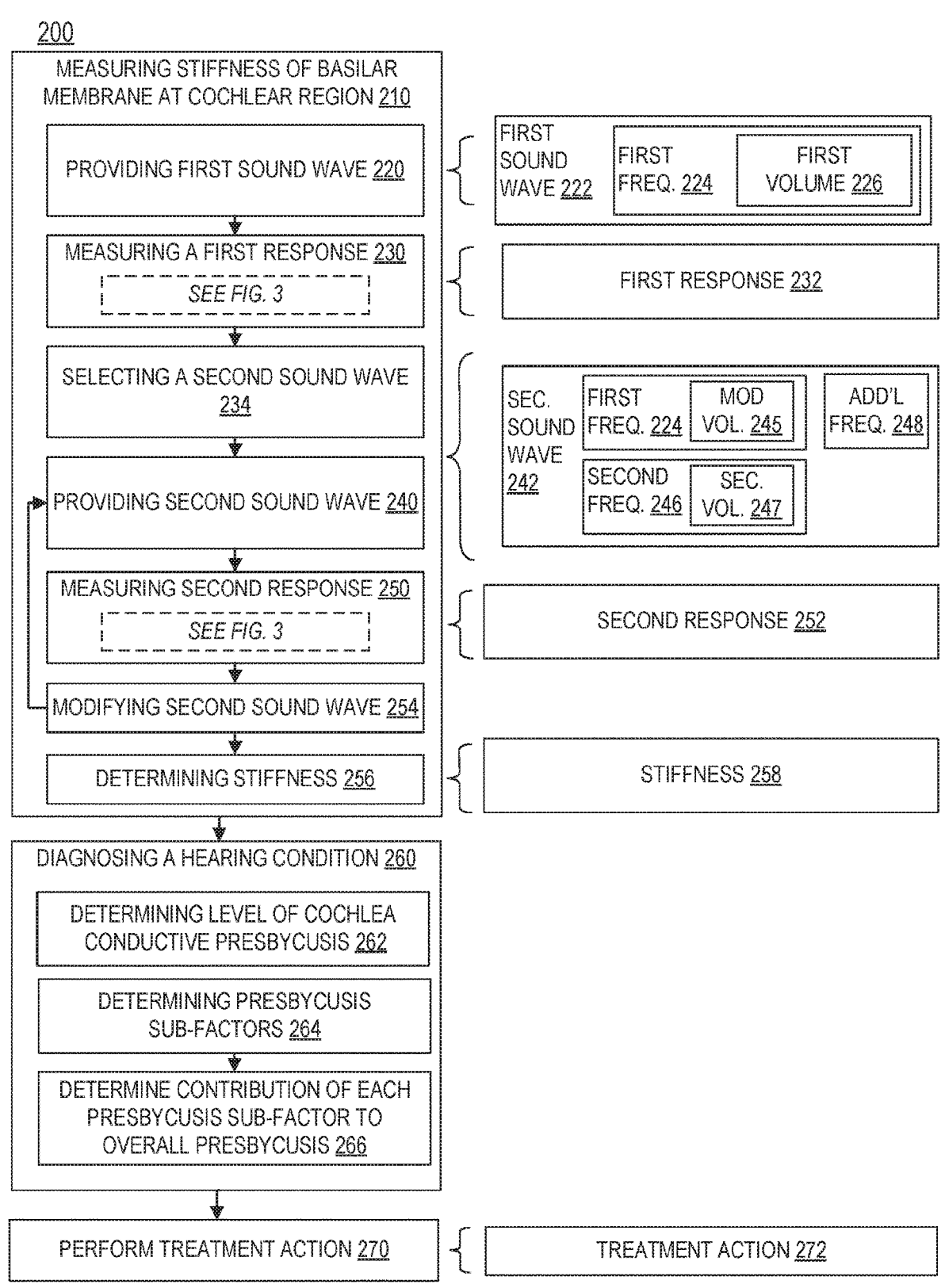
FIG. 2 illustrates an example method.
Figure 9:
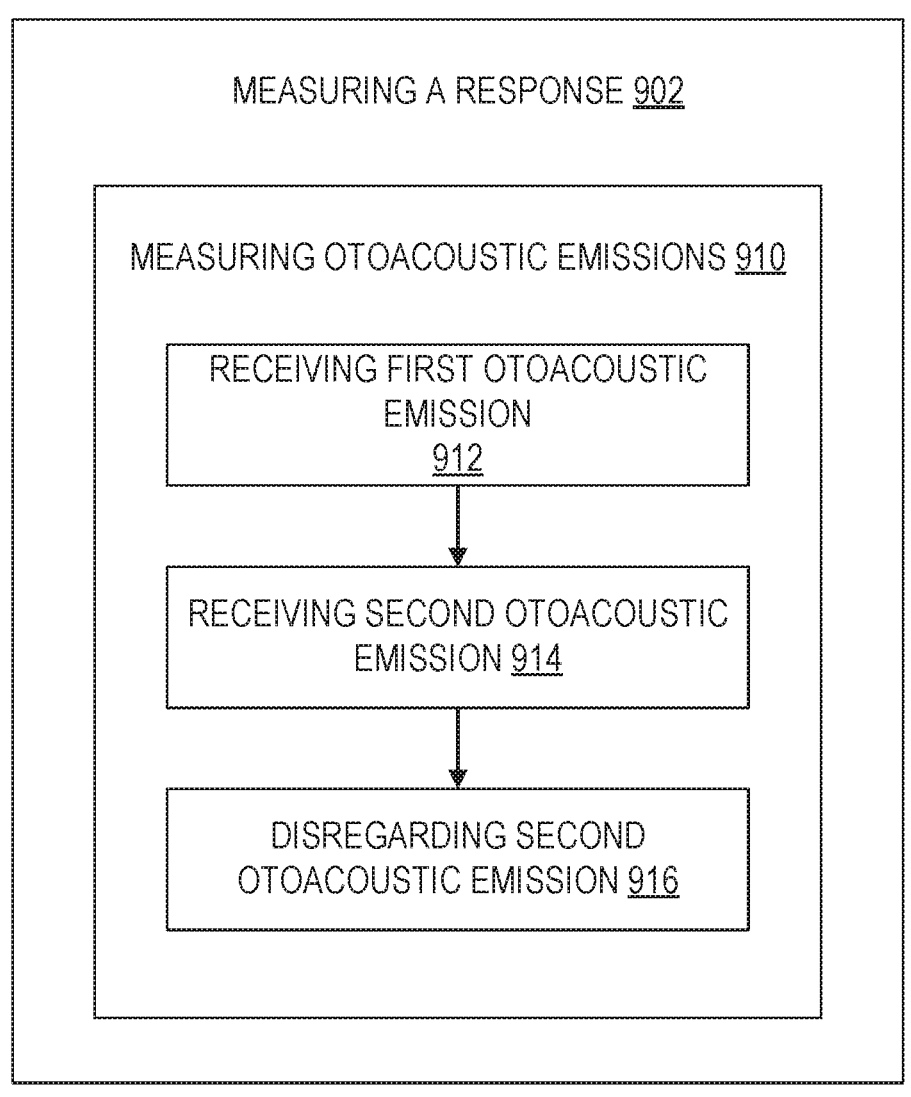
FIG. 9 illustrates an example method for measuring a response.
Figure 10:
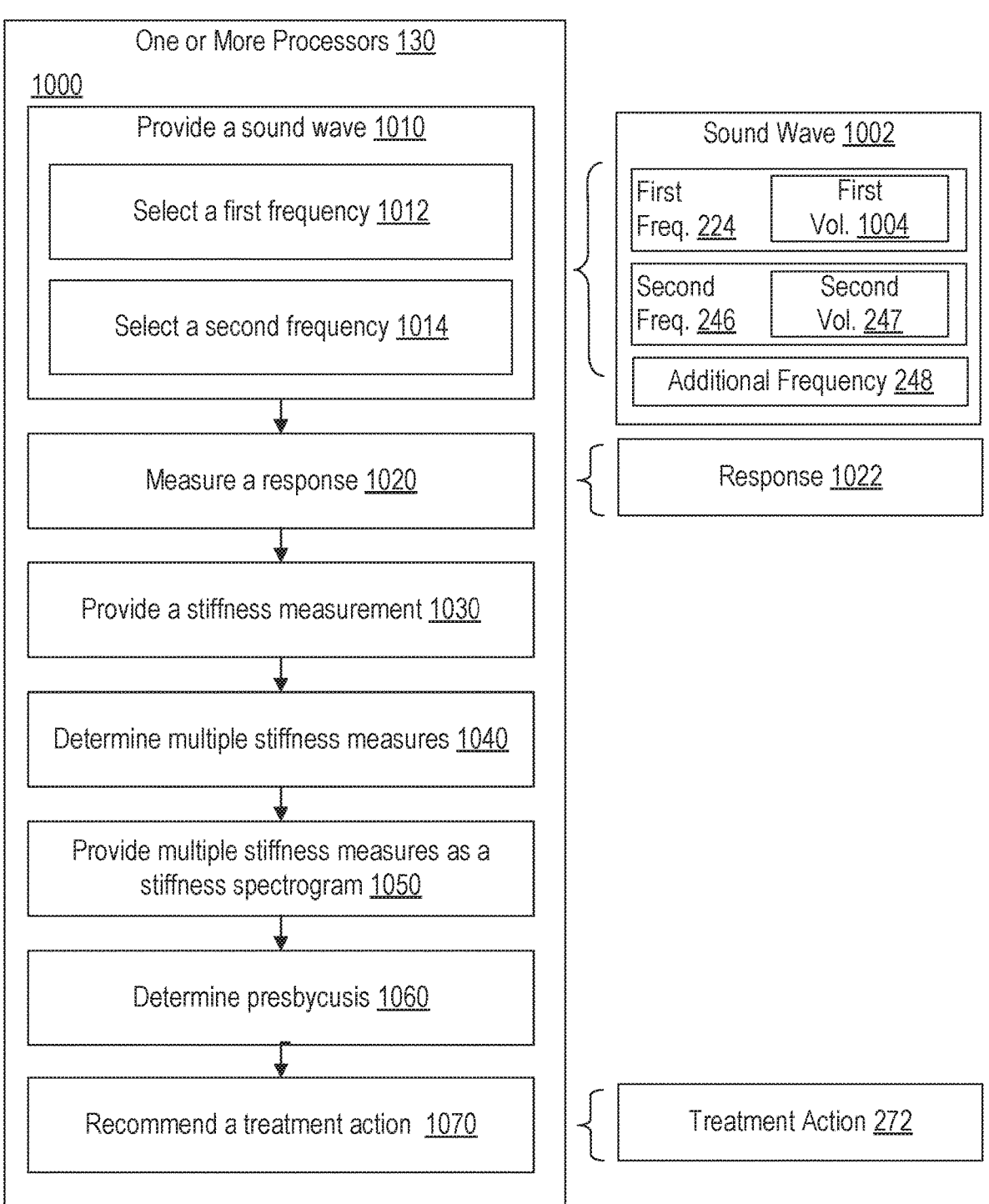
FIG. 10 illustrates one or more processors configured to perform a method.

The components of the system 100 are usable to perform one or more methods or operations, including those described in relation to FIGS. 2, 9, and 10.

Example Method

FIG. 2 illustrates an example method 200 that includes measuring a stiffness of a basilar membrane, diagnosing a hearing condition, and performing a treatment action. The method 200 can begin with operation 210.

Operation 210 includes measuring stiffness of a basilar membrane at a first region 10 of a subject's cochlea. The operation 210 can include one or more sub-operations. The illustrated operation 210 includes operations 220, 230, 234, 240, 250, 254, and 256. Other implementations can include more, fewer, or different operations. The measuring of the stiffness can be repeated for one or more additional regions of the cochlea.

Operation 220 includes providing a first sound wave 222 to the cochlea, such as via the stimulator 110. The illustrated example of the first sound wave 222 includes a first fre-quency 224 that has a first volume 226. The first sound wave 222 is provided in any of a variety of ways, such as via a receiver, a speaker, a headphone, or a vibratory actuator. In an example, the first volume 226 is a volume above an otoacoustic emission threshold. The otoacoustic emission threshold can be an actual threshold or predicted threshold (e.g., based on typical responses from similar individuals) for the subject that, when satisfied, causes an otoacoustic emission.

In an example, the first sound wave 222 is an initial sound wave used to gather initial data regarding a first region 10 of the subject's cochlea. The first region 10 can also be referred to as the target region 10 or the tested region 10 and refers to the region of the subject's cochlea (e.g., the region of the basilar membrane of the cochlea) that resonates (or is believed to resonate) with the first frequency 224.

Operation 230 includes measuring a first response 232, such as via the sensor 120. The first response 232 is a response to the first sound wave 222. In an example, the first response 232 is a detected otoacoustic emission produced by the subject's cochlea in response to the first sound wave 222. The first response 232 can be a direct or indirect measure-ment of the subject's outer hair cell receptor potential or firing of spiral ganglion neurons. In some examples, the first response 232 is measured using evoked compound action potential or electrocochleography. Additional techniques for measuring a response are described in relation to FIG. 9. In some examples, the first response 232 is used as a baseline against which subsequent responses are measured. A non-limiting example of providing a sound wave and receiving a response is shown in FIG. 3.

Figure 3:
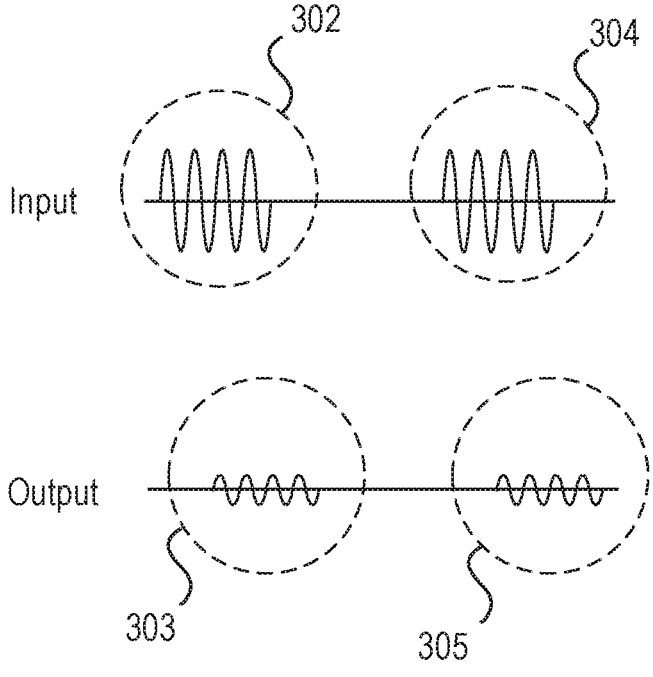
FIG. 3 illustrates an example sound waves having one frequency provided as input and a resulting output.

FIG. 3 illustrates an example of providing input to a subject's auditory system and detecting a response. As illustrated, a first sound wave 302 results in receiving a slightly delayed first signal 303 and a second sound wave 304 results in receiving a slightly delayed second signal 305. In an example, the first sound wave 302 and the second sound wave 304 are provided in the form of air- or bone-conducted vibrations and the first signal 303 and the second signal 305 are received as otoacoustic emissions detected by a microphone. In other examples, the first signal 303 and the second signal 305 are detected as electrical signals, such as detected by an electrode.

Returning to FIG. 2, operation 234 includes selecting a second sound wave 242, such as using the one or more processors 130. The illustrated example of the second sound wave 242 includes the first frequency 224 at a modified volume 245, a second frequency 246 at a second volume 247, and one or more optional, additional frequencies 248.

The first frequency 224 of the second sound wave 242 is selected to be substantially the same as the first frequency 224 of the first sound wave 222. In an example, the first frequency 224 is within a margin of error or tolerance of the stimulator 110 being used to generate the sound waves 222, 242. Generally, the first frequency 224 of the second sound wave 242 is configured to stimulate the first region 10, which is the same region of the subject's cochlea stimulated by the first sound wave 222.

The volume of the first frequency 224 is selected to be the same as or different from the first volume 226. As illustrated, the volume of the first frequency 224 is a modified volume 245. The modified volume 245 is modified relative to the first volume 226, such as by being higher or lower than the first volume 226. In an example, the modified volume 245 is selected to be above an otoacoustic emission threshold (an actual or assumed otoacoustic emission threshold for the subject). In an example, the modified volume 245 is more than 5%, 10%, 15%, 20%, 25%, 30%, 35%, 40%, 45%, or 50% different (e.g., higher or lower) compared to the first volume 226. In at least some examples, the modified volume 245 is selected to be a volume that will result in a response to the second sound wave 242 being substantially the same as a response 232 to the first sound wave 222, such as is described in more detail below. In other examples, the first frequency 224 has a volume that is substantially the same as the first volume 226 (e.g., within a tolerance or margin of error of the stimulator 110 that produced the second sound wave).

The second frequency 246 is a frequency configured to bias the first region 10 of the cochlea. In an example, the second frequency 246 is selected to be a frequency that is lower than the first frequency 224. For instance, the second frequency 246 is a frequency that is configured to resonate a second region 20 of the cochlea different from the first region 10, yet still affect the first region 10 such that the second frequency 246 constructively or destructively biases the first region 10. In an example, the operation 234 includes selecting the second sound wave 242 such that a measured second response (see operation 250, below) to the second sound wave 242 is within a threshold amount of the first response 232. In an example, the second frequency 246 is configured to constructively bias the first region 10, and in another example, the second frequency 246 is configured to destructively bias the first region 10. In an example, the second volume 247 is selected to be below an actual or believed otoacoustic emission threshold for the subject.

In some examples, the second frequency 246 is selected to have one or more additional frequencies 248 having their own volumes or volumes similar to the second volume 247 or modified volume 245. In an example, the one or more additional frequencies 248 are selected. In an example, the one or more additional frequencies 248 are harmonic. In an example, the one or more additional frequencies 248 are selected to contribute to a substantially square wave shape of the second sound wave 242, such as a square wave shape over which the first frequency 224 is provided as a burst.

Operation 240 includes providing the second sound wave 242, such as via the stimulator 110. In examples, the second sound wave 242 is generated such that the first frequency 224 is provided as a short burst at a particular portion of the second frequency 246, rather than being substantially continuous for the duration of the second sound wave 242. For instance, the first frequency can be a burst proximate the crest or trough of the second frequency 246 component of the second sound wave 242, such that the second frequency 246 provides constructive or destructive bias, respectively, during the time at which the first frequency 224 resonates the first region 10.

In an example, the second sound wave 242 is provided to the cochlea such that a measured second response (see operation 250) to the second sound wave 242 is within a threshold amount of the first response 232. In some examples, an initial providing of the second sound wave 242 results in such a measured second response 252. In other examples, the initial providing of the second sound wave 242 does not result in such a measured second response 252. The second sound wave 242 can be modified until a measured second response 252 is achieved that is within a threshold amount of the first response 232. Such a modification is described in relation to operation 254, below.

Operation 250 includes measuring a second response 252. The second response 252 is a response to the provided second sound wave 242. In an example, the second response 252 is measured in substantially the same way as the first response 232. In another example, the second response 252 is measured such in such a way that the second response 252 includes the subject's response to the first frequency 224 component of the second sound wave 242 but not the second frequency 246 component. Such a technique is described in more detail in relation to FIG. 3. In some examples, the second response 252 includes a component relating to a response to the first frequency 224 and a component relating to a response to the second frequency 246.

Operation 254 includes modifying the second sound wave 242. For example, the operation includes modifying the second sound wave 242 until a measured second response 252 to the second sound wave 242 is within the threshold amount of the first response 232. Example modifications include modifying the modified volume 245 of the first frequency 224 or modifying the second volume 247 of the second frequency 246. For instance, responsive to the second response 252 being lower (e.g., less intense) than the first response 232, the modified volume 245 is increased. Responsive to the second response 252 being higher (e.g., more intense) than the first response 232, the modified volume 245 is decreased. Following the modifying of the second sound wave 242, the modified second sound wave 242 can be provided, with the flow of the method 400 returning to operation 240.

Figure 4:
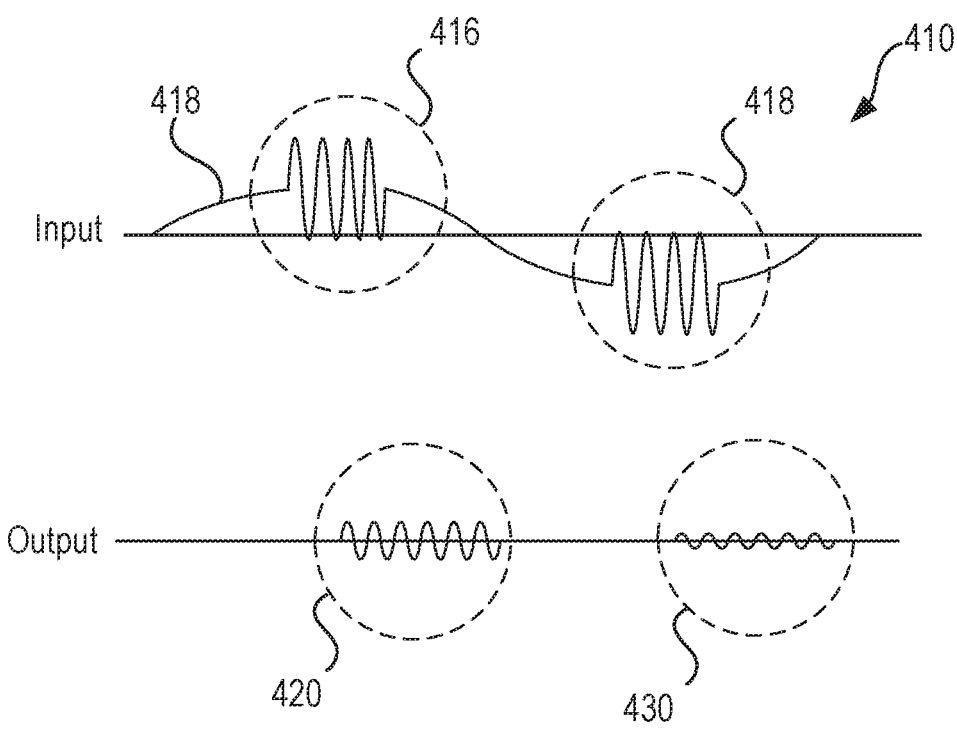
FIG. 4 illustrates an example sound waves having first and second frequencies provided as input and resulting outputs.

A non-limiting example of a second sound wave 242 and second responses 252 thereto are shown in FIG. 4.

FIG. 4 illustrates an example sound wave 410 provided as input and a resulting output. The sound wave 410 includes a first frequency component 412 having a relatively higher frequency than a second frequency 414 component. As illustrated, the sound wave 410 includes first frequency section A 416 and first frequency section B 418 proximate a crest and a trough of the second frequency 414 component of the sound wave 410, respectively. As illustrated, the first frequency section A 416 and first frequency section B 418 are configured as high-frequency bursts over particular portions of the second frequency 414 component.

As illustrated, the second frequency component 414 results in substantially no detectable output from the subject. The first frequency section A 416 results in a first output section 420 having a relatively higher amplitude than the second section output section 430 resulting from the first frequency section B 418. The first frequency section A 416 is proximate a crest of the second frequency component 414, which results in the crest of the second frequency component 414 providing a constructive bias to the first region 10 (e.g., the region that the first frequency section A 416 resonates with) and therefore results in a higher amplitude of output in the first output section 420. The first frequency section B 418 proximate a trough of the second frequency component 414 results in a destructive bias to the first region 10 and therefore results in a lower amplitude of output in the second output section 430.

Figures 5, 6:
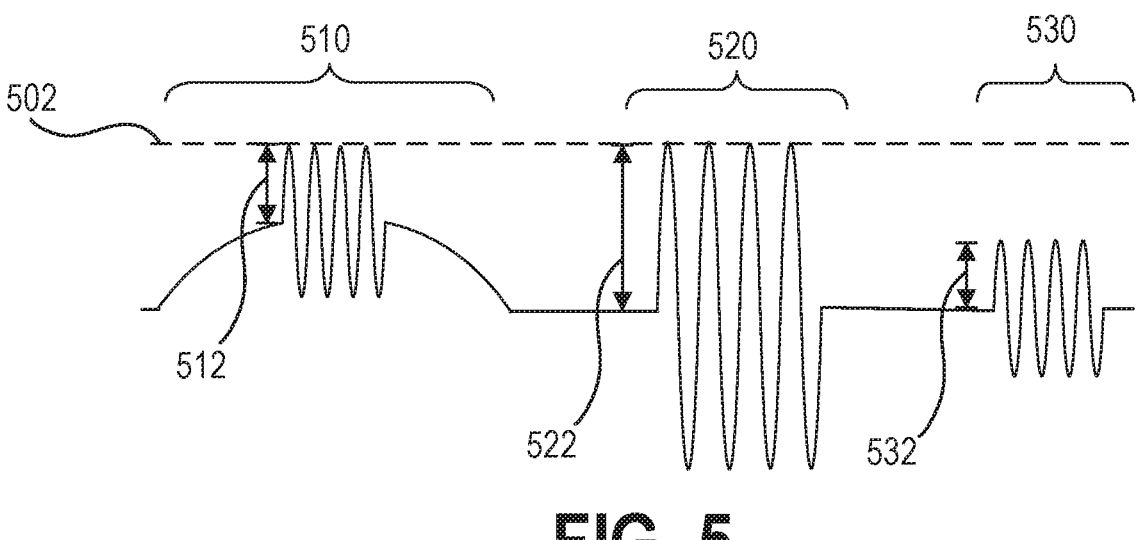
FIG. 5 illustrates a first sound wave, a second sound wave, and a third sound wave relative to an activation threshold.
FIG. 6 illustrates first, second, and third sound waves, each having respective amplitudes, all relative to an activation threshold.

Continued examples of combinations of high and low frequencies are shown in FIGS. 5 and 6.

FIG. 5 illustrates a first sound wave 510, a second sound wave 520, and a third sound wave 530 relative to an activation threshold 502. The first sound wave 510 is similar to the sound wave 410 of FIG. 4 and includes a high frequency section located at a crest of a low frequency section, thereby being constructively biased. The first sound wave 510 includes a first amplitude 512. The second sound wave 520 includes an unbiased high frequency section having a second amplitude 522 sufficient to cause the second sound wave 520 to reach the activation threshold 502. The third sound wave 530 includes an unbiased high frequency section having a third amplitude 532. The first amplitude 512 and the third amplitude 532 are substantially similar and approximately half of the second amplitude 522. As illustrated, the constructive bias of the first sound wave 510 is sufficient to cause the sound wave 510 to reach the activation threshold 502 despite the first amplitude 512 being approximately half of the second amplitude 522. The third sound wave 530 has approximately the same amplitude as the first sound wave 510 but is unbiased and is therefore unable to reach the activation threshold.

FIG. 6 illustrates a first sound wave 610 having a first amplitude 612, a second sound wave 620 having a high frequency section having a second amplitude 622, and a third sound wave 630 having a high frequency section having a third amplitude 632, all relative to and reaching an activation threshold 602.

The first sound wave 610 is unbiased and reaches the activation threshold 602. The second sound wave 620 includes a low-frequency section that constructively biases the high frequency section in such a way that the high-frequency section reaches the activation threshold 602 despite the second amplitude 622 being substantially half of the first amplitude 612. The third sound wave 630 includes a low-frequency section that destructively biases the high frequency section in such a way that the high-frequency section reaches the activation threshold 602 with the third amplitude 632 being substantially double the first amplitude 612.

In some examples, the response from the subject's auditory system is or is related to the firing of the subject's Spiral Ganglion (SPG). The sound waves provided to the auditory system can affect the voltage potential of the recipient's outer hair cells. Where the voltage potential reaches a certain threshold, the SPG fires. An example of this process is shown in FIGS. 7 and 8.

Figures 7, 8:
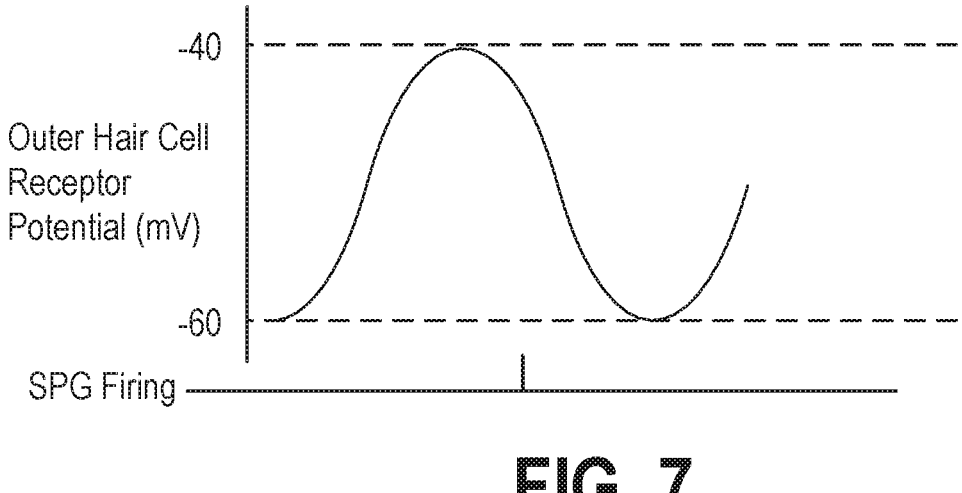
FIG. 7 illustrates outer hair cell receptor potential over time.
FIG. 8 illustrates outer hair cell receptor potential over time.

FIG. 7 illustrates outer hair cell receptor potential over time in response to an input signal (e.g., a sound wave). The outer hair cell receptor potential is approximately centered around −50 mV and shifts potential between approximately −60 mV and −40 mV as a result of the input signal. When the receptor potential is approximately −40 mV, the SPG neuron fires shortly after. In some examples, this firing is detected as the response 232, 252.

FIG. 8 illustrates outer hair cell receptor potential over time in response to an input signal. The potential is approximately centered around −55 mV due to being destructively biased (e.g., as a result of a high frequency burst being provided over a trough of a low frequency), resulting in shifts in potential of between approximately −65 mV and −45 mV. Because the receptor potential is less than approximately-40 mV, there is no firing of SPG neurons.

Returning to FIG. 2, operation 256 includes determining stiffness 258. In an example, determining the stiffness 258 includes determining a stiffness 258 of a basilar membrane of the cochlea (e.g., the stiffness of the first region 10) based on one or more differences between the first sound wave 222 and the second sound wave 242. In many examples, the stiffness 258 is derived from an extent to which the second frequency 246 component of the second sound wave 242 biased the membrane at the first region 10. This extent is determinable based on the differences between the second response 252 (which was in response to a sound wave 242 that had the biasing second frequency 246) and the first response 232 (which was in response to the first sound wave 222 that lacked the biasing second frequency 246). The difference can be determined based on or expressed as a ratio between the first volume 226 and the modified volume 245, where the modified volume 245 is a volume needed to overcome the bias to result in substantially similar first and second responses 232, 252. In another example, the stiffness 258 is measured as the ratio of input signal (dB) to electrical neural response (uV), where the input signal corresponds to the modified volume 245 and the electrical neural response corresponds to the second response 252.

In an example, determining the stiffness 258 includes providing data to an artificial intelligence framework (e.g., as described in FIG. 11) and receiving an output in response that indicates the value of stiffness 258. The data provided to the artificial intelligence framework can include data describing the first sound wave 222 and the second sound wave 242, such as the first frequency 224, the first volume 226, the modified volume 245, the second volume 247, and data regarding one or more additional frequencies 248. The artificial intelligence framework can be trained to receive such data as input and provide a stiffness measure as output.

In an example, the stiffness 258 is a measure of the first region 10 of the cochlea. In another example, the stiffness 258 is an actual or estimated measurement of the stiffness of the subject's cochlea overall. For instance, the stiffness 258 may be a value generated based on an average or other statistical process applied to one or more other obtained stiffnesses 258.

Operation 260 includes diagnosing a hearing condition. In examples the diagnosing includes diagnosing the extent of the hearing condition (e.g., an amount of hearing loss). In an example, the hearing condition is diagnosed based on the stiffness 258 of the basilar membrane being above a diagnostic threshold. In some examples, the diagnosing can include one or more of operations 262, 264, and 266.

Operation 262 includes determining a level of cochlea conductive presbycusis. The level is determined based on the measured second response 252. Cochlea conductive presbycusis relates to basilar membrane stiffening, thus measures related to stiffness are usable to determine a level of cochlea conductive presbycusis. For example, the level of cochlea conductive presbycusis is determined based on the stiffness 258 as calculated based on the measured second response 252. The determining can be performed in any of a variety of ways. In some examples, the determining is based on one or more equations that take at least the stiffness 258 as a variable and produce, as an output, a level of cochlea conductive presbycusis. In some examples, the determining is based on a lookup table, where levels of cochlea conductive presbycusis are indexed to measures of stiffness 258. In some examples, an artificial intelligence technique is used to determine the level of cochlea conductive presbycusis, such as by providing the stiffness 258 as input to an artificial intelligence framework and receiving, as output, the determined level of cochlea conductive presbycusis.

In addition to or instead of determining the level of cochlea conductive presbycusis, the method 200 determines a level of overall presbycusis. The level of overall presbycusis can be determined based on contributing factors to the overall presbycusis. For instance, the following equation can be used:

$$Presbycusis(dB\ HL)=Y*Strial+\Phi*Sensory+X*Neural+\Pi*Conductive,$$

where the input variables Strial, Sensory, Neural and Conductive represent the measure of their respective presbycusis subfactor. For example, Conductive can, in one example, correspond to the measure of the stiffness of the basilar membrane represented in the ratio between the first volume 226 and the modified volume 245. In an example, Neural can correspond to the measure of the auditory brainstem response. In this example linear multi-regression model, the coefficients Y, $\Phi$, X, and $\Pi$ can be determined, through calculation or experimentation, to provide the estimate of the Presbycusis through the input variables. For example, if the patient had Presbycusis which was solely due to conductive presbycusis (stiffening of the basilar membrane), then the Strial, Sensory and Neural variables would not contribute to the model, and the resultant Presbycusis would be a function of $\Pi*$Conductive. A variety of techniques can be used to determine the values of Y, $\Phi$, X, and $\Pi$. Examples are described below in relation to operations 264 and 266. And similarly, a variety of techniques or transforms can be used to determine Strial, Sensory, Neural, and Conductive, to provide a linear variable type for this simple variable model.

Operation 264 includes determining a plurality of presbycusis sub-factors, such as a level of the plurality of sub-factors. In an example, the presbycusis sub-factors include strial presbycusis, sensory presbycusis, neural presbycusis, and cochlea conductive presbycusis. Other sub-factors can be used. Levels of strial presbycusis and sensory presbycusis are determined based on testing outer hair cell function, such as by measuring otoacoustic emissions or through the use of audiograms (e.g., as evidenced by loss at 2-4 KHz). The relative contribution of strial and sensory presbycusis is determinable based on delta auditory brain response compared with delta otoacoustic emission threshold. Auditory brainstem response can be used to determine neural presbycusis. The cochlea conductive presbycusis is determined using one or more of the techniques described in operation 262. In an example, otoacoustic emissions, auditory brainstem response, and the determined stiffness are used to determine the values of Y, $\Phi$, X, and $\Pi$.

Operation 266 includes determining contribution of each of the plurality of presbycusis sub-factors to overall presbycusis. With the plurality of presbycusis sub-factors determined in operation 264, the relative contribution of each factor is determined. For example, the extent to which each factor contributes to overall presbycusis is determined.

Operation 270 includes performing a treatment action 272. The treatment action 272 can be determined based on the measured plurality of presbycusis sub-factors of operation 264. Example treatment actions 272 include recommending a pharmacological substance, recommending a hearing aid, recommending a bone conduction device, recommending a cochlear implant, recommending a hearing aid fitting, recommending a bone conduction fitting, other recommendations, or combinations thereof.

In an example, responsive to determining that an amount of sensory presbycusis is above a predetermined threshold, a hearing aid is prescribed as the treatment action 272. In an example, responsive to determining that an amount of strial presbycusis is above a predetermined threshold, a voltage pump or vascular dilation drug can be prescribed as the treatment action 272. In an example, responsive to determining that an amount of inner hair cell loss, the prescription of DNA therapy can be prescribed or recommended as the treatment action.

In an example, responsive to determining that a level of overall presbycusis or levels of one or more sub-factors passes a threshold, a subject that is already a recipient of an auditory prosthesis, is recommended one or more changes in settings to address the presbycusis. For example, the level of overall presbycusis indicates that the recipient is losing residual hearing and the treatment action 272 is to change one or more settings of an existing auditory prosthesis.

As described above, various techniques can be used to measure a response (e.g., the first response 232 and the second response 252). Additional techniques for measuring a response are described in relation to FIG. 9.

Measuring a Response

FIG. 9 illustrates a method for measuring a response 902. Measuring the response 902 can include measuring one or more of auditory brainstem response, an electrocochleogram, and electrical compound action potentials, such as with the sensor 130. In an example, the response is measured with one or more electrodes of a cochlear implant or a trans-tympanic electrode. In an example, the response is measured with a microphone.

The method 902 includes operation 910, which includes measuring otoacoustic emissions. The otoacoustic emissions can include delta-otoacoustic emissions or dual-tone-otoacoustic emissions.

In some examples, the otoacoustic emissions are measured in response to the second sound wave 242 that includes the first frequency 224 and the second frequency 246. In many examples, the second frequency 246 is used to bias the first region 10 of the cochlea where the first frequency 224 resonates. The second frequency 246 resonates with the second region 20 of the cochlea that is different from the first region 10. Thus, while the second frequency 246 may result in generating an otoacoustic emission or other response by resonating with the second region 20 of the subject's auditory system, the response may not be relevant to determining qualities of the first region 10 of the cochlea where the first frequency 224 resonates. As a result, in some examples, the second frequency 246 of the second sound wave 242 is configured to affect the target region of the subject's cochlea while nonetheless being below an otoacoustic emissions threshold. In other examples, the second frequency 246 of the second sound wave 242 is sufficient to cause otoacoustic emissions, but the response provoked by the second frequency 246 is disregarded. The operations are operations 912, 914, and 916.

Operation 912 includes receiving a first otoacoustic emission. The first otoacoustic emission corresponds to the first frequency 224 component of the second sound wave 242. Because the first frequency 224 is higher than the second frequency 246, the first frequency 224 resonates at a more basal location of the cochlea. Resonating at the more basal first region 10 results in the otoacoustic emission corresponding to the first frequency 224 being produced first.

Operation 914 includes receiving a second otoacoustic emission. The second otoacoustic emission can correspond to the second frequency 246 component of the second sound wave 242. Because the second frequency 246 is lower than the first frequency 224, the second frequency 246 resonates at a more apical location of the cochlea. Resonating at the more apical second region 20 results in the otoacoustic emission corresponding to the second frequency 246 being produced after the first otoacoustic emission. Thus, the timing of receipt of the otoacoustic emissions can be used to distinguish them as relating to the first frequency 224 or the second frequency 246. In other examples, the emissions are distinguished via other techniques, such as based on other characteristics of the responses.

Operation 916 includes disregarding the second otoacoustic emission. The disregarding can be performed in any of a variety of ways. For instance, the second otoacoustic emission is received but not saved or stored for later use. As another example, the sensor 120 that receives the otoacoustic emission is turned off or otherwise configured to not generate output based on the second otoacoustic emission. In a still further example, data is generated based on the second otoacoustic emission but the data is flagged or otherwise distinguished as being related to the second otoacoustic emission such that the data relating to the second otoacoustic emission is not used.

Measuring a Response

FIG. 10 illustrates one or more processors 130 configured to perform a method 1000 that includes various operations. The one or more processors 130 can be communicatively coupled to memory 140 having stored thereon instructions that so configure the one or more processors 130. For instance, the memory 140 can include instructions 142 thereon that, when executed by the one or more processors 130, cause the one or more processors 130 to perform the one or more operations herein. In an example, the operations include operation 1010, operation 1020, 1030, 1040, 1050, 1060, and 1070.

Operation 1010 includes to provide a sound wave 1002. As illustrated, the sound wave 1002 includes a first frequency 224 at a first volume 1004, a second frequency 246 at a second volume 247, and an additional frequency 248. In an example, the operation 1010 can include one or more aspects of those described in relation to operation 240. In some examples, operation 1010 includes operations 1012 and 1014.

Operation 1012 includes to select the first frequency 224. In an example, the operation 1012 includes selecting a first frequency configured to activate the first region 10. For example, a target region of the subject's cochlea is chosen (e.g., based on a diagnostic plan or symptoms of the subject) as the first region 10 and the first frequency 224 is selected to target the first region 10 based on the ability of the first frequency 224 to resonate at the first region 10. In some examples, the operation 1012 further includes to select the first volume 1004 of the first frequency 224. In an example, the first volume 1004 corresponds to the modified volume 245 of the second sound wave 242 of FIG. 2 and can be selected in a similar manner. In an example, the operation 1012 can include one or more aspects of those described in relation to operation 234 and 254.

Operation 1014 includes to select a second frequency 246. In an example, the operation 1014 includes selecting a second frequency 246 configured to bias the first region 10, such as constructively bias or destructively bias the first region 10. In an example, the operation 1014 can include one or more aspects of those described in relation to operation 234 and 254.

Operation 1020 includes to measure a response 1022. The response 1022 is to the provided sound wave 1002. In an example, the operation 1020 includes one or more aspects similar to those described in relation to operation 250.

Operation 1030 includes to provide a stiffness measurement. The stiffness measurement can be a measurement of the stiffness of the first region 10 and can be based on the response 1022. In an example, the stiffness is determined using one or more techniques described in relation to operation 256. The stiffness measurement can then be provided to the subject or a clinician using any of a variety of techniques, such as by displaying the result on a display screen or by audibly providing the stiffness measurement Operation 1040 includes to determine multiple stiffness measurements. For instance, at least operations 1010, 1020, and 1030 are repeated for multiple different values of the first frequency 224 to determine the multiple stiffness measurements for different regions in the subject's cochlea. In an example, the multiple stiffness measurements are a range of frequencies lower than the original first frequency 224 used to determine the original stiffness measurement before the operations are repeated. The multiple stiffness measurements can be used to determine an overall stiffness of the basilar membrane of the subject's cochlea (e.g., based on averaging or performing another statistical process on the multiple stiffness measurements).

Operation 1050 includes to provide multiple stiffness measures as a stiffness spectrogram. For example, the multiple stiffness measurements obtained in operation 1040 can be provided to a user (e.g., the subject or a clinician). In an implementation, the x-axis of the spectrogram corresponds to frequency and the y-axis of the spectrogram corresponds to stiffness.

Operation 1060 includes to determine presbycusis. For example, the presbycusis can include cochlea conductive presbycusis and can be determined based on the response 1022. In addition, the presbycusis can include strial presbycusis, sensory presbycusis, and neural presbycusis. The operation 1060 can include one or more aspects similar to those described above in relation to operation 260.

Operation 1070 includes to recommend a treatment action 272. For example, the operation 1070 can include one or more aspects similar to those described in relation to operation 270.

Example Artificial Intelligence Model

Figure 11:
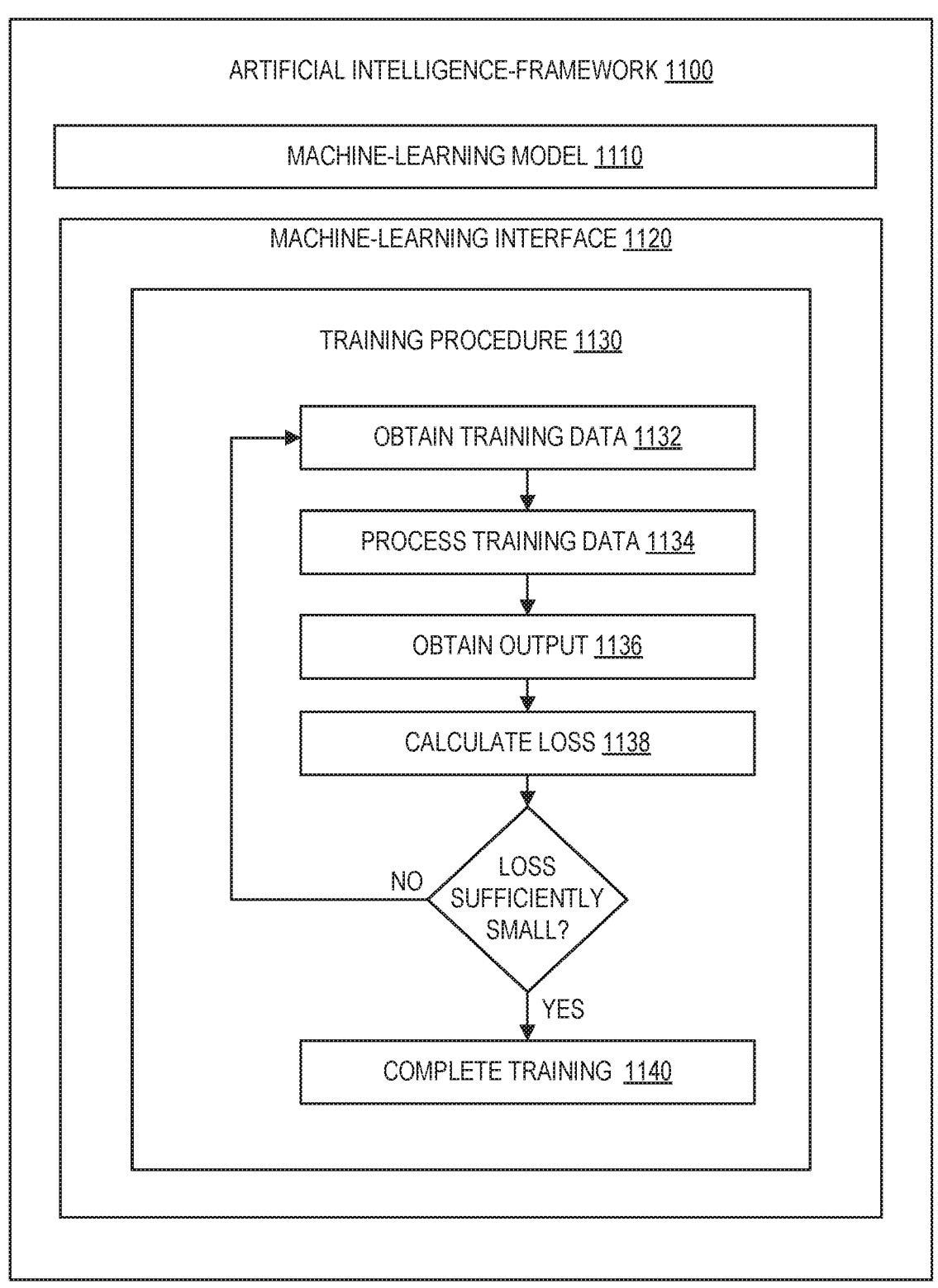
FIG. 11 illustrates an example artificial intelligence framework usable with examples herein.

FIG. 11 illustrates an example artificial intelligence framework 1100 usable with examples herein. In an example, the computing device 102 stores and operates the artificial intelligence framework 1100. The artificial intelligence framework 1100 includes software instructions and associated data that implement artificial intelligence capabilities.

In examples, the artificial intelligence framework 1100 defines implementations of one or more different artificial intelligence techniques. For example, the artificial intelligence framework 1100 defines a decision tree (e.g., the nodes of the decision tree and the connections therebetween).

In the illustrated example, the artificial intelligence framework 1100 includes a machine-learning model 1110 and a machine-learning interface 1120. One or more aspects of the artificial intelligence framework 1100 can be implemented with machine-learning toolkits or libraries, such as: TEN-SORFLOW by GOOGLE INC. of Mountain View, California; OPENAI GYM by OPENAI of San Francisco, California; or MICROSOFT AZURE MACHINE LEARNING by MICROSOFT CORP. of Redmond, Washington.

The machine-learning model 1110 is a structured representation of the learning, such as how learning is achieved and what has been learned. For example, where the machine-learning model 1110 includes a neural network, the machine-learning model 1110 can define the representation of the neural network (e.g., the nodes of the neural network, the connections between the nodes, the associated weighs, and other data), such as via one or more matrices or other data structures.

The machine-learning interface 1120 defines a software interface used in conjunction with the machine-learning model 1110. For example, the machine-learning interface 1120 can define functions, processes, and interfaces for providing input to, receiving output from, training, and maintaining the machine-learning model 1110.

In some examples, the machine-learning interface 1120 requires the input data to be preprocessed. In other examples, the machine-learning interface 1120 can be configured to perform the preprocessing. The preprocessing can include, for example, placing the input data into a particular format for use by the machine-learning model 1110. For instance the machine-learning model 1110 can be configured to process input data in a vector format and the data provided for processing can be converted into such a format via the preprocessing. In an example, the interface provides functions that convert the provided data into a useful format and then provide the converted data as input into the machine-learning model 1110.

The machine-learning interface 1120 can define a training procedure 1130 for preparing the machine-learning model 1110 for use. The artificial intelligence framework 1100 can be trained or otherwise configured to receive data as input and provide an output based thereon. For example, the machine-learning model 1110 can be trained to receive data or parameters described herein as input and provide, as output, an indication of whether the provided data is indicative of an amount of stiffness or an extent of presbycusis. The training procedure 1130 can begin with operation 1132.

Operation 1132 includes obtaining training data. The training data is typically a set of human- or machine-curated data having known training input and desired training output usable to train the machine-learning model 1110. In examples herein, the training data can include curated responses 1022 from many different individuals or that is artificially-created and actual or expected output of the machine-learning model 1110 for that data. For example, the training data can include particular responses 1022 associated with measurements of stiffness. Following operation 1132, the flow can move to operation 1134.

Operation 1134 includes processing the training data. Processing the training data includes providing the training data as input into the machine-learning model 1110. In examples, the training data can be provided as input into the machine-learning model 1110 using an associated machine-learning interface 1120. Then the machine-learning model 1110 processes the input training data to produce an output.

Following operation 1134, the flow can move to operation 1136. Operation 1136 includes obtaining the output from the machine-learning model 1110. This can include receiving output from a function that uses the machine-learning model 1110 to process input data. Following operation 1136, the flow can move to operation 1138.

Operation 1138 includes calculating a loss value. A loss function can be used to calculate the loss value, such as based on a comparison between the actual output of the machine-learning model 1110 and the expected output (e.g., the training output that corresponds to the training input provided). Any of a variety of loss functions can be selected and used, such as mean square error or hinge loss. Attributes of the machine-learning model 1110 (e.g., weights of connections in the machine-learning model) can be modified based on the loss value, thereby training the model.

If the loss value is not sufficiently small (e.g., does not satisfy a threshold), then the flow can return to operation 1132 to further train the machine-learning model 1110. This training process continues for an amount of training data until the loss value is sufficiently small. If the loss value is sufficiently small (e.g., less than or equal to a predetermined threshold), the flow can move to operation 1140.

Operation 1140 includes completing the training. In some examples, completing the training includes providing the artificial intelligence framework 1100 for use in production. For example, the artificial intelligence framework 1100 with the trained machine-learning model 1110 can be stored on the computing device 102 or at another location for use. In some examples, prior to providing the artificial intelligence framework 1100 for use, the trained machine-learning model 1110 is validated using validation input-output data (e.g., data having desired outputs corresponding to particular inputs that are different from the training data), and after successful validation, the artificial intelligence framework 1100 is provided for use.

The machine-learning model 1110 can include multiple different types of machine-learning techniques. For example, the machine-learning model 1110 can define multiple different neural networks, decision trees, and other machine-learning techniques and their connections therebetween. For instance, output of a first neural network can flow to the input of a second neural network with the output therefrom flowing into a decision tree to produce a final output.

Example Devices

Technology described herein can result in the subject of the test being prescribed a device, such as a cochlear implant, an electroacoustic device, a percutaneous bone conduction device, a passive transcutaneous bone conduction device, an active transcutaneous bone conduction device, a middle ear device, a totally-implantable auditory device, a mostly-implantable auditory device, an auditory brainstem implant device, a hearing aid, a tooth-anchored hearing device, other auditory prostheses, and combinations of the foregoing (e.g., binaural systems that include a prosthesis for a first ear of a recipient and a prosthesis of a same or different type for the second ear). In some examples, techniques described herein can be relevant to consumer devices, such as a personal sound amplification product. Further, in some examples, such devices can be used to stimulate and record the responses. Further still, a subject of the tests described herein may be a recipient of such devices and techniques used herein are used to determine presbycusis of residual hearing. In still further examples, stiffness and amount of presbycusis can be used to modify stimulation settings of such devices.

Among the devices are cochlear implant systems, which are described in more detail in relation to FIG. 12, below, and bone conduction devices, which are described in more detail in relation to FIG. 13, below.

Example Device—Cochlear Implant

Figure 12:
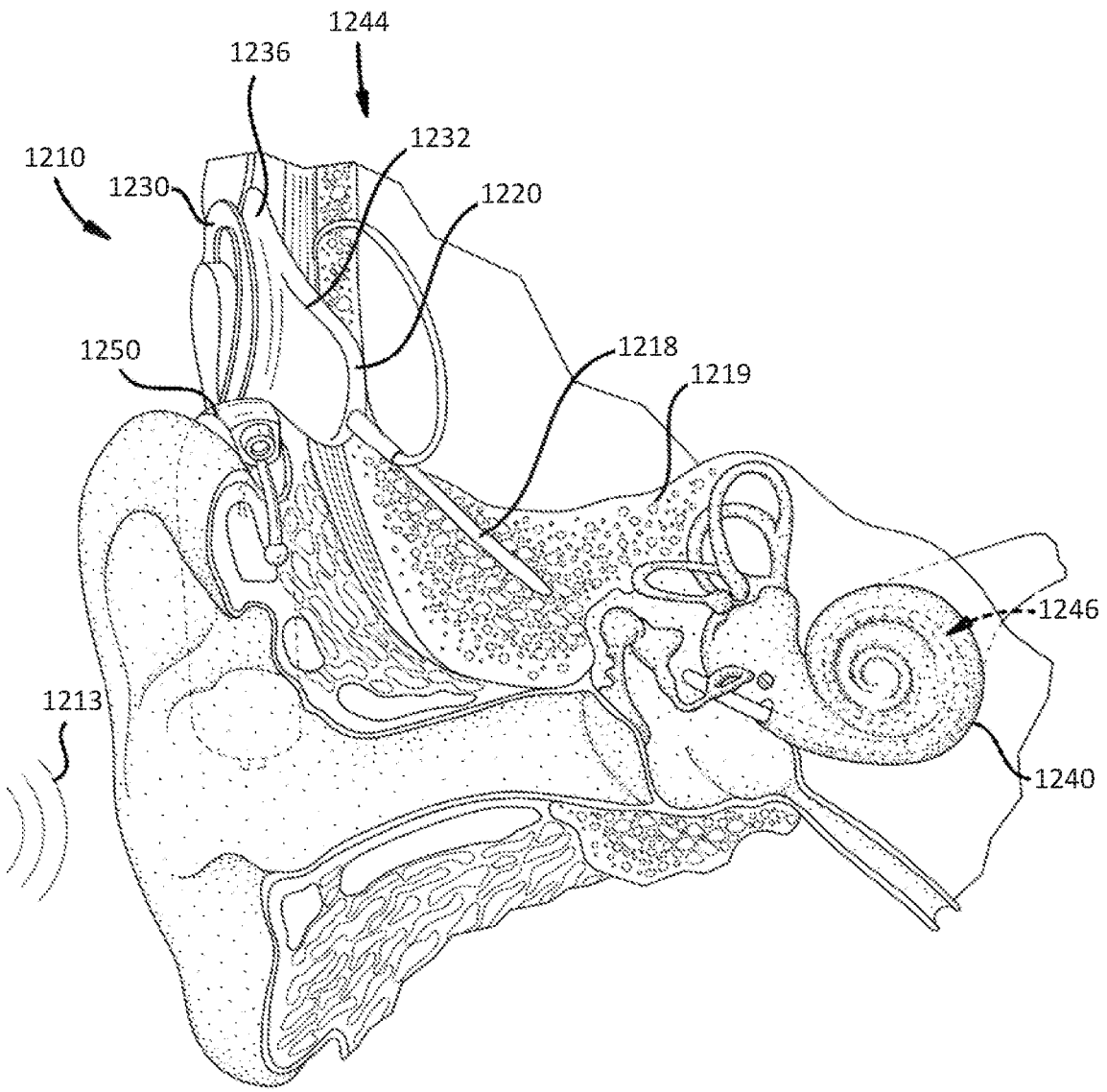
FIG. 12 illustrates an example cochlear implant system.

FIG. 12 illustrates an example cochlear implant system 1210 that can be used with examples herein. For example, the cochlear implant system 1210 can be used to implement the computing device 102 or one or both of the stimulator 110 and the sensor 120. The cochlear implant system 1210 includes an implantable component 1244 typically having an internal receiver/transceiver unit 1232, a stimulator unit 1220, and an elongate lead 1218. The internal receiver/transceiver unit 1232 permits the cochlear implant system 1210 to receive signals from and/or transmit signals to an external device 1250. The external device 1250 can be a button sound processor worn on the head that includes a receiver/transceiver coil 1230 and sound processing components. Alternatively, the external device 1250 can be just a transmitter/transceiver coil in communication with a behind-the-ear device that includes the sound processing components and microphone.

The implantable component 1244 includes an internal coil 1236, and preferably, an implanted magnet fixed relative to the internal coil 1236. The magnet can be embedded in a pliable silicone or other biocompatible encapsulant, along with the internal coil 1236. Signals sent generally correspond to external sound 1213. The internal receiver/transceiver unit 1232 and the stimulator unit 1220 are hermetically sealed within a biocompatible housing, sometimes collectively referred to as a stimulator/receiver unit. Included magnets can facilitate the operational alignment of an external coil 1230 and the internal coil 1236 (e.g., via a magnetic connection), enabling the internal coil 1236 to receive power and stimulation data from the external coil 1230. The external coil 1230 is contained within an external portion. The elongate lead 1218 has a proximal end connected to the stimulator unit 1220, and a distal end 1246 implanted in a cochlea 1240 of the recipient. The elongate lead 1218 extends from stimulator unit 1220 to the cochlea 1240 through a mastoid bone 1219 of the recipient. The elongate lead 1218 is used to provide electrical stimulation to the cochlea 1240 based on the stimulation data. The stimulation data can be created based on the external sound 1213 using the sound processing components and based on sensory prosthesis settings.

In certain examples, the external coil 1230 transmits electrical signals (e.g., power and stimulation data) to the internal coil 1236 via a radio frequency (RF) link. The internal coil 1236 is typically a wire antenna coil having multiple turns of electrically insulated single-strand or multi-strand platinum or gold wire. The electrical insulation of the internal coil 1236 can be provided by a flexible silicone molding. Various types of energy transfer, such as infrared (IR), electromagnetic, capacitive and inductive transfer, can be used to transfer the power and/or data from external device to cochlear implant. While the above description has described internal and external coils being formed from insulated wire, in many cases, the internal and/or external coils can be implemented via electrically conductive traces.

Example Device—Bone Conduction Device

Figure 13:
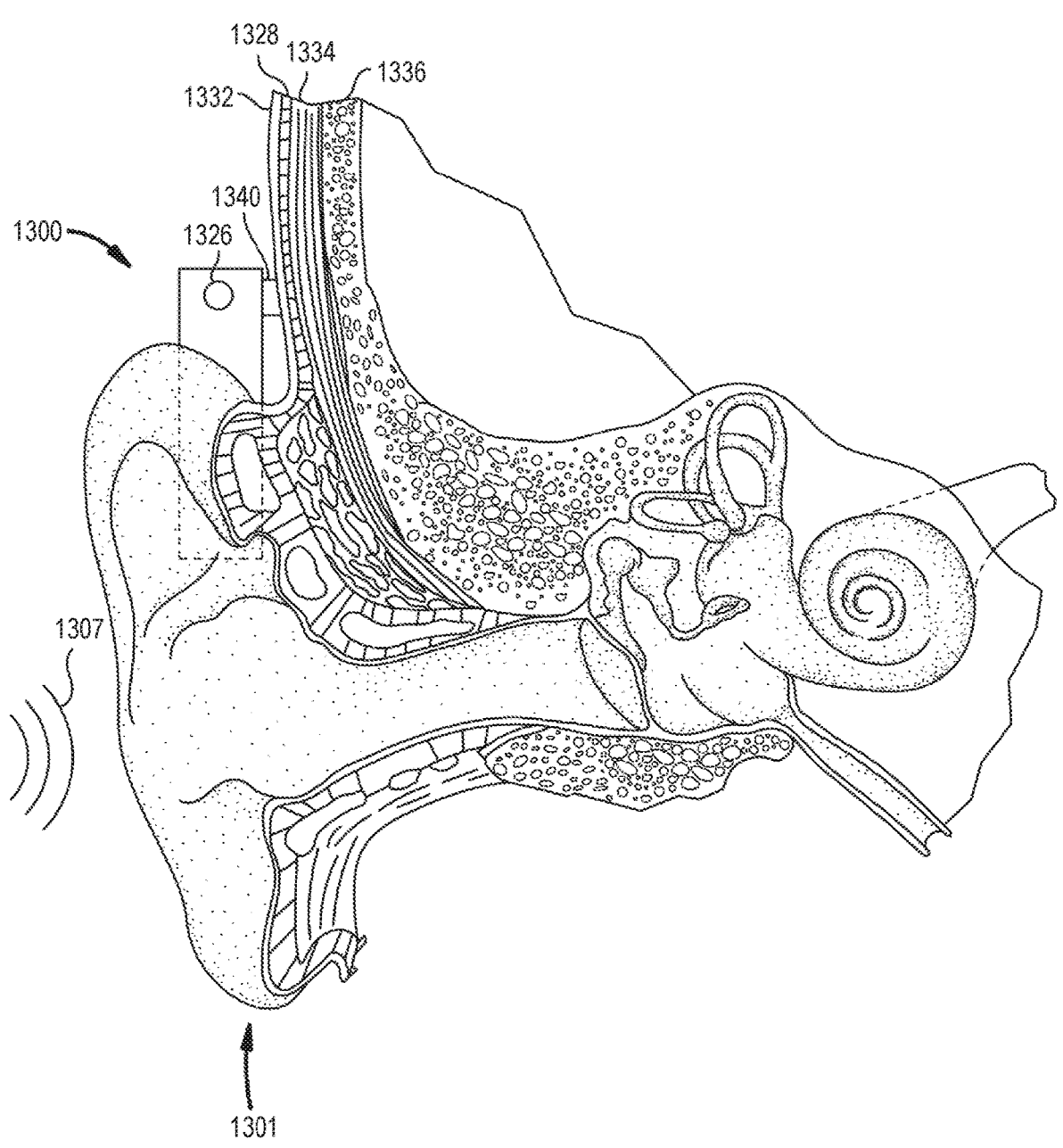
FIG. 13 illustrates an example bone conduction device.

FIG. 13 is a view of an example of a bone conduction device 1300 that can benefit from use of the technologies disclosed herein. For example, the bone conduction device 1300 can be used to implement the computing device 102 or one or both of the stimulator 110 and the sensor 120. The bone conduction device 1300 is positioned behind an outer ear 1301 of a recipient of the device. The bone conduction device 1300 includes a sound input element 1326 to receive sound signals 1307. The sound input element 1326 can be a microphone, telecoil or similar. In the present example, the sound input element 1326 is located, for example, on or in the bone conduction device 1300, or on a cable extending from the bone conduction device 1300. Also, the bone conduction device 1300 comprises a sound processor (not shown), a vibrating electromagnetic actuator and/or various other operational components.

More particularly, the sound input element 1326 converts received sound signals into electrical signals. These electrical signals are processed by the sound processor. The sound processor generates control signals that cause the actuator to vibrate. In other words, the actuator converts the electrical signals into mechanical force to impart vibrations to a skull bone 1336 of the recipient. The conversion of the electrical signals into mechanical force can be controlled by input received from a user.

The bone conduction device 1300 further includes a coupling apparatus 1340 to attach the bone conduction device 1300 to the recipient. In the illustrated example, the coupling apparatus 1340 is attached to an anchor system (not shown) implanted in the recipient. An example anchor system (also referred to as a fixation system) includes a percutaneous abutment fixed to the skull bone 1336. The abutment extends from the skull bone 1336 through muscle 1334, fat 1328 and skin 1332 so that the coupling apparatus 1340 can be attached thereto. Such a percutaneous abutment provides an attachment location for the coupling apparatus 1340 that facilitates efficient transmission of mechanical force. Another example anchor system includes the use of a headband, strap, or other device to hold a vibratory plate (configured to impart vibrations to the recipient's skull) proximate the recipient's skull without the need to use an implanted anchor. In yet another example anchor system, one or more magnets are implanted beneath the recipient's skin 1332 and magnetic attraction between the bone conduction device 1300 and the magnets are used to retain the bone conduction device 1300.

Further Example Treatments

In addition to or instead of the use of devices to treat presbycusis, other therapies or treatments can be used, such as pharmaceutical products. For example, a vascular dilation drug can be prescribed. DNA therapy can be prescribed or recommended as a treatment for inner hair cell loss. Or devices which contain pharmaceuticals in a combination device may be prescribed.

As should be appreciated, while particular uses of the technology have been illustrated and discussed above, the disclosed technology can be used with a variety of devices in accordance with many examples of the technology. The above discussion is not meant to suggest that the disclosed technology is only suitable for implementation within systems akin to that illustrated in the figures. In general, additional configurations can be used to practice the processes and systems herein and/or some aspects described can be excluded without departing from the processes and systems disclosed herein.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and processes to the particular aspects described. Accordingly, additional configurations can be used to practice the methods and systems herein and/or some aspects described can be excluded without departing from the methods and systems disclosed herein.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure. Further, the disclosed processes can be repeated.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

What is claimed is:

1. A method, comprising:
providing one or more sound waves to an inner ear of a recipient, wherein the one or more sound waves include a first component having a first frequency configured to activate a tissue region of the inner ear, and a second component having a second frequency that is lower than the first frequency and is configured to bias the tissue region;
measuring a response to the provided one or more sound waves; and
determining a stiffness of a basilar membrane at a region of the inner ear based on the measured response.

2. The method of claim 1, further comprising:
determining a level of cochlea conductive presbycusis based on the measured response.

3. The method of claim 1, further comprising:
determining a plurality of presbycusis sub-factors, wherein cochlea conductive presbycusis is one of the plurality of the presbycusis sub-factors; and
determining contribution of each of the plurality of presbycusis sub-factors to overall presbycusis.

4. The method of claim 3, further comprising:
performing a treatment action based on the plurality of presbycusis sub-factors.

5. The method of claim 4, wherein performing the treatment action includes:
recommending a pharmacological substance, a hearing aid for the recipient, a bone conduction device for the recipient, a cochlear implant for the recipient, an operational adjustment to a hearing aid associated with the recipient, or an operational adjustment to a bone conduction device associated with the recipient.

6. The method of claim 1, further comprising:
performing the measuring of stiffness for one or more additional regions of the inner ear.

7. The method of claim 1, wherein measuring the response includes measuring otoacoustic emissions.

8. The method of claim 7, wherein measuring otoacoustic emissions includes:
receiving a first otoacoustic emission corresponding to the first frequency;
receiving a second otoacoustic emission corresponding to the second frequency; and
disregarding the second otoacoustic emission.

9. The method of claim 1, wherein the second frequency is configured to at least one of constructively bias the region or destructively bias the region.

10. The method of claim 1, wherein the one or more sound waves comprise a first sound wave and a second sound wave, and wherein the method comprises:
providing the first sound wave at a first volume to the inner ear, wherein the first sound wave comprises the first component having the first frequency;
measuring a first response to the first sound wave;
providing the second sound wave to the inner ear such that a measured second response to the second sound wave is within a threshold amount of the first response, wherein the second sound wave includes:
a component having the first frequency delivered at a modified volume relative to the first volume; and
a second component having the second frequency, delivered at a second volume; and
determining the stiffness of the basilar membrane of the inner ear based on one or more differences between the first sound wave and the second sound wave.

11. The method of claim 10, wherein providing the second sound wave to the inner ear includes:
providing the second sound wave to the inner ear; and
modifying the second sound wave until a measured second response to the second sound wave is within the threshold amount of the first response.

12. The method of claim 11, wherein modifying the second sound wave until a measured second response to the second sound wave is within the threshold amount of the first response includes:
modifying the modified volume of the first frequency; or
modifying the second volume of the second frequency.

13. The method of claim 10, wherein the second sound wave includes multiple additional frequencies that are lower in frequency than the first frequency.

14. The method of claim 13, wherein the multiple additional frequencies are harmonic.

15. The method of claim 10, wherein measuring the first response includes measuring the first response with an electrocochleogram.

16. The method of claim 10, further comprising:

diagnosing a hearing condition of the inner ear based on the stiffness of the basilar membrane being above a diagnostic threshold.

17. The method of claim 16, wherein the hearing condition is cochlea conductive presbycusis.

18. The method of claim 10, wherein determining the stiffness of the basilar membrane of the inner ear based on the one or more differences between the first sound wave and the second sound wave includes determining a ratio between the first volume and the second volume.

19. The method of claim 10, wherein at least one of the first volume or the modified volume is a volume above an otoacoustic emission threshold.

20. A system comprising:

an electroacoustic transducer configured to provide at least one sound wave to an inner ear of a recipient, the at least one sound wave having:

a first frequency component having a first frequency configured to activate a tissue region;

a second frequency component having a second frequency that is lower than the first frequency configured to bias the tissue region;

a response sensor configured to measure a response to the provided sound wave; and one or more processors configured to cause the electroacoustic transducer to provide the at least one sound wave and to determine a stiffness of a basilar membrane at a region of the inner ear based on the response measured by the response sensor.

21. The system of claim 20, wherein the one or more processors are further configured to:

provide a stiffness measurement for a tissue region based on the response.

22. The system of claim 20, wherein the response sensor includes one or more electrodes.

23. The system of claim 20, wherein the response sensor is an electrocochleography monitor.

24. The system of claim 20, wherein the one or more processors are further configured to:

select the second frequency to constructively bias the tissue region.

25. The system of claim 20, wherein the one or more processors are further configured to:

select the second frequency to destructively bias the tissue region.

26. The system of claim 20, wherein the one or more processors are further configured to:

determine multiple stiffness measures using a range of frequencies lower than the first frequency.

27. The system of claim 26, wherein the one or more processors are further configured to:

provide the multiple stiffness measures as a stiffness spectrogram.

28. The system of claim 20, wherein the one or more processors are further configured to:

determine cochlea conductive presbycusis based on the response; and recommend a treatment action based on the cochlea conductive presbycusis.

29. The system of claim 20, wherein the system includes memory having instructions thereon that, when executed, so configure the one or more processors, and wherein the one or more processors are configured to measure at least one of strial presbycusis, sensory presbycusis, neural presbycusis, or cochlea conductive presbycusis.

* * * * *